United States Patent [19]
Kuniyuki

[11] Patent Number: 5,106,761
[45] Date of Patent: Apr. 21, 1992

[54] METHOD FOR DETECTING MOLECULES IN A LIQUID MEDIUM

[75] Inventor: Andrew H. Kuniyuki, Berwyn, Pa.

[73] Assignee: International Canine Genetics, Inc., Malvern, Pa.

[21] Appl. No.: 322,563

[22] Filed: Mar. 13, 1989

[51] Int. Cl.$^5$ .................. G01N 33/549; G01N 33/546
[52] U.S. Cl. ...................... 436/533; 422/57; 422/58; 436/532; 436/805; 436/810
[58] Field of Search ............ 422/56, 57, 58, 59, 422/60, 69, 70; 260/659, 660, 203, 286; 436/805, 810, 824, 518, 519; 435/805, 5, 37

[56] References Cited

U.S. PATENT DOCUMENTS

| | | | |
|---|---|---|---|
| 3,825,410 | 7/1974 | Bagshawe | 436/57 |
| 3,862,303 | 1/1975 | Anderson | 436/534 |
| 3,888,629 | 6/1975 | Bagshawe | 422/61 |
| 4,094,647 | 5/1978 | Deutsch et al. | 436/810 |
| 4,098,876 | 7/1978 | Piasio et al. | 436/536 |
| 4,138,474 | 2/1979 | Updike | 436/810 |
| 4,168,146 | 9/1979 | Grubb et al. | 436/810 |
| 4,205,058 | 5/1980 | Wagner et al. | 436/810 |
| 4,235,601 | 11/1980 | Deutsch et al. | 422/56 |
| 4,366,241 | 12/1982 | Tom et al. | 422/56 |
| 4,376,110 | 3/1983 | David et al. | 436/513 |
| 4,690,907 | 9/1987 | Hibino et al. | 422/56 |

Primary Examiner—David L. Lacey
Assistant Examiner—Thomas E. Daley
Attorney, Agent, or Firm—Limbach & Limbach

[57] ABSTRACT

The invention is a method for the detection of molecules in a liquid medium involving the trapping of solid support conjugates. The reactants of the present invention are drawn upward through the device by capillary action against the force of gravity.

3 Claims, 4 Drawing Sheets 5,106,761

METHOD FOR DETECTING MOLECULES IN A LIQUID MEDIUM

BACKGROUND OF THE INVENTION

1. Field of the Invention

This inventions relates to a method and device for the performance of assays that detect molecules; in particular, a method and device for the performance of assays that detect molecules in a liquid medium by virtue of their binding to other molecules.

2. Description of the Prior Art

The association of particular molecules with the health and condition of the body has made it important to develop methods and devices for the detection of molecules that are sensitive, efficient and inexpensive. One approach to such methods and devices is to take advantage of affinities of particular molecules for other molecules. Such affinities have been observed with many types of molecules and are, perhaps, best characterized between nucleic acids (DNA-DNA, DNA-RNA, etc.) and between proteins (enzyme-substrate, receptor-hormone, etc.).

Antibodies are among the most frequently used molecules with affinity for other molecules. The molecules reacting and binding with antibodies are collectively referred to as antigens. Antigens can be of many different types of molecules with many different functions. Prior art uses of antibodies and antigens include both the measurement of antigen with antibody and the measurement of antibody with antigen.

When contemplating the design of a method or device utilizing molecules that react and bind to one another, the primary technical consideration is the means by which bound molecules are separated from unbound reactants. There are a number of approaches to separating bound from unbound reactants known in the prior art.

One approach is to take advantage of the selective absorbing characteristics of a chromatographic matrix. For example, in U.S. Pat. No. 4,205,058, bound and unbound reactants are separated on the basis of size as they passed through a silica gel by capillary action. There are a number of disadvantages to such an approach, however. First, chromatographic matrices that separate molecules by size have molecular dimension requirements necessary for adequate separation. These molecular dimension requirements will change depending on the particular size of the molecules to be separated. Thus, one single matrix will not be adequate for every type of separation. Second, a sizing system must have enough travel distance for the molecules to effect a separation. In the typical case where the matrix is housed in a column, for example, the column must be of sufficient length to allow the unbound reactants to travel away from the bound reactants.

Another approach to separating bound from unbound reactants is to attach and immobilize binding molecules on a solid support so as to create a solid support conjugate. The solid support conjugate with one type of binding molecule is allowed to react with free molecules of a different type. Once the molecule-molecule complex has formed, the mobile, unbound reactants can be separated by exerting a force on the reaction mixture. For example, in U.S. Pat. No. 3,862,303, bound and unbound reactants are separated by using latex beads as a solid support and by centrifugation of the reaction mixture on a density gradient. This method has the disadvantage of the expense and inconvenience of centrifugation equipment.

Another solid support approach is disclosed in U.S. Pat. No. 4,138,474. Bound and unbound reactants are separated in a syringe device by using antibody-containing gel particles as a solid support and by forcing unbound reactants past a barrier through which the gel particles cannot flow. This approach has the disadvantage that the flow rate is controlled by mechanical action and, thus, may not be uniform. Nonuniform flow rates can impact the degree of binding of the reactants and change the sensitivity of the assay.

Still other solid support approaches are disclosed in U.S. Pat. Nos. 4,094,674, 4,168,146, 4,235,601, and 4,366,241. Reactants are separated by using immobilized antibody in an immunoreactive zone as a solid support and by flowing reactants past the immunoreactive zone. These methods have the disadvantage that binding occurs at the time the reactants are separated. Thus, the time allowed for binding is fixed by the flow rate. The amount of time allowed for binding dramatically impacts assay sensitivity.

The present invention presents a solid support approach to the separation of bound and unbound reactants that is sensitive, efficient and inexpensive. The invention does not utilize a sizing system, requires no expensive equipment or mechanical force, and does not separate bound and unbound reactants at the time of binding.

Objects and advantages other than those above set forth will be apparent from the following description when read in connection with the accompanying figures.

SUMMARY OF THE INVENTION

The present invention is a method and device for the performance of assays that detect unconjugated molecules in a liquid medium by virtue of their binding to solid support conjugates. The device comprises a means for receiving the liquid medium, a means for drawing the liquid medium against the force of gravity through said receiving means, a means for trapping the solid support conjugates present in the liquid medium, and a means for detecting the unconjugated molecules bound to the trapped solid support conjugates.

The method comprises contacting the liquid medium with an assay device, drawing the liquid medium against the force of gravity through the device, trapping the solid support conjugates, and detecting the unconjugated molecules bound to the trapped solid support conjugates.

DESCRIPTION OF THE INVENTION

Figure 1:
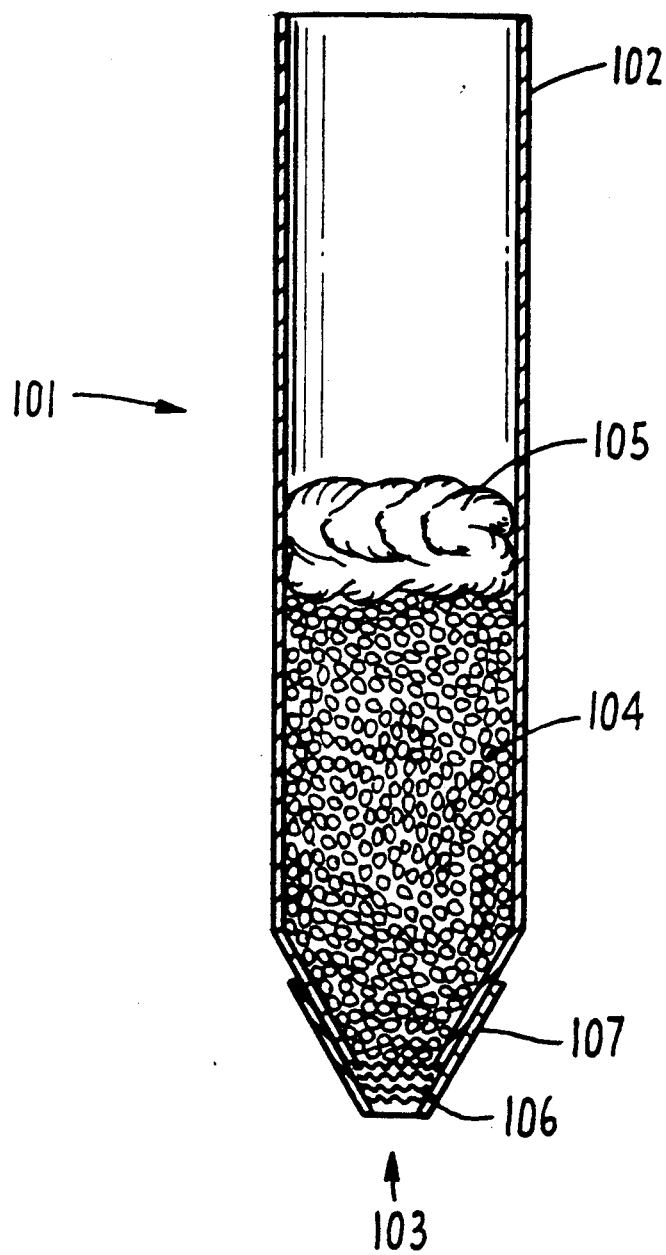
FIG. 1 is a side view of one embodiment of the device of the invention.

The present invention presents a solid support approach to the separation of bound and unbound reactants. The invention is both a method and device for the performance of assays that detect unconjugated molecules in a liquid medium by virtue of their binding to solid support conjugates.

The device comprises a means for receiving the liquid medium containing unconjugated molecules bound to the solid support conjugates, a means for drawing the liquid medium against the force of gravity through the receiving means, a means for trapping the solid support conjugates, and a means for detecting trapped, unconjugated molecules bound to the solid support conjugates.

It is contemplated that the means for receiving liquid comprises at least one aperture or orifice in a container. The container can be made out of any material suitable for holding liquid, such as plastic or glass. It also may be of any shape and dimensions.

The aperture(s) may also be of any dimensions. However, because the liquid medium is drawn through the aperture(s) against the force of gravity by a drawing means, the aperture(s) would be contemplated to be at or near the bottom of the container.

The drawing means might be by any number of physical or mechanical forces. For example, the liquid medium might drawn upward with a pump or vacuum. The preferred drawing means, however, is contemplated to be capillary action.

Capillary action might be supplied by any material having absorbing properties. It is contemplated that the absorbing material is housed in the container. Nonetheless, absorbing material that, itself, serves as a container is within the scope of the invention.

It is contemplated that a web or net barrier provides the means for trapping the solid support conjugates. The web may simply be a semipermeable membrane. The web may also be a woven fabric or a network of fibers. The trapping may be achieved by physical entanglement or may be achieved by charge interactions with the web material. The invention also contemplates ionic and nonionic chemical trapping.

The number of means are contemplated for detecting trapped, unconjugated molecules bound to the solid support conjugates. One approach is to use labelled, unconjugated molecules to compete for binding with unlabelled unconjugated molecules. The preferred approach is to use additional binding molecules with affinity for the molecules bound to the solid support conjugates. Such a binding molecule might be protein, though it need not be limited to proteins. If it is a protein, it might be a hormone, a receptor, an enzyme, an antibody, or any other protein with the appropriate affinity and specificity.

Whatever the functional nature of the binding molecule, it is intended that it directly or indirectly provide a detection signal when bound to the molecules that are bound to the solid support conjugates. An example of a direct signal is provided when the additional binding molecules are themselves labelled. Such a label might be radioactive or fluorescent. An example of an indirect signal is provided when the additional binding molecules contain a functional group that becomes activated upon the addition of an activating reagent. Such a functional group might exist on the additional binding molecules naturally (i.e. bifunctional binding molecules), might be added by chemical reactions prior to use of the additional binding molecules (e.g., enzyme coupling), or might be added after the additional binding molecules (e.g., binding of an antibody to the additional binding molecules).

The method comprises receiving the liquid medium containing the unconjugated molecules bound to the solid support conjugates, drawing the liquid medium against the force of gravity through the receiving means, trapping the solid support conjugates and the unconjugated molecules bound to the solid support conjugates, and detecting the trapped, unconjugated molecules bound to the solid support conjugates.

To receive the liquid medium, it is contemplated that the device described above would be placed in contact with a liquid medium containing the reaction mixture. This might be done by hand or this might by done in an automated manner such as in a machine.

Following contact of the device with the liquid medium, it is preferred that the liquid will be drawn into the device against the force of gravity by the drawing means of the device without the need for further manual effort. Of course, other embodiments, such as those where contact of the device and the liquid medium does not automatically bring the absorbing material into the appropriate relationship to immediately draw the liquid upward, may require additional manipulations of the elements of the device.

Experimental

In order to further describe the present invention, the following experiments and examples were carried out to demonstrate the efficacy of the device and method.

All quantities labelled percent (%) are grams per 100 milliliters, unless otherwise indicated. All weights are given in grams (g) or milligrams (mg), all concentrations are given as millimolar (mM) or micromolar ($\mu$M) and all volumes are given in liters (L), milliliters (ml) or microliters ($\mu$l) unless otherwise indicated.

EXAMPLE 1

FIG. 1 shows one embodiment of the device of the present invention. The device comprises a container (101) with an upper end (102) and a liquid receiving end (103). The container (101) houses absorbent material (104). The absorbent material (104) is retained in the container (101) by virtue of a plug (105) at the upper end (102) and a web (106) at the liquid receiving end (103). The web (106) is maintained in position at the liquid receiving end (103) of the container (101) by a collar (107).

With this embodiment, a straight stem column of constant diameter works best as the container (101). An inexpensive embodiment utilizes a standard laboratory pipet made of glass or plastic. Laboratory pipet typically have a tapered, open end and an untapered, open end. In this embodiment, the tapered, open end serves as the liquid receiving end (103) and the untapered, open end serves as the upper end (102) of the device. The collar (107) can be fashioned by cutting off the tapered, open end of another pipette. The plug (105) can be made of cotton.

The absorbent material (104) may be made of any substance having absorbent properties. In the preferred embodiment, the absorbent material (104) is diatomaceous earth. Diatomaceous earth provides the advantages of matrix uniformity, high capillary flow rate, packing ease, and goodness-of-fit (adapting to a variety of shapes).

It is desirable to pack the absorbent material (104) in a manner that results in close compaction against the web (106) to ensure capillary transfer. Diatomaceous earth, it should be noted, tends to settle after the initial filling. The end settling point can be reached by periodic tapping.

EXAMPLE 2

A Fisher transfer pipet (Fisher Catalog No. 13-711-7) is cut back to create a larger tip having about 5-6 mm O.D. The bulb is cut off to form an open-ended tube for a container (101). A second pipet is used to create a tapered fitted collar (107). A section of the tapered tip is cut off having a 7 mm O.D. at the smaller end. This collar (107) slides back about 6 mm from the tip of the pipet tube.

A 1 cm$^2$ piece of glass fiber filter paper (934-AH, Whatman Catalog No. 1827-830 [8.3 cm × 14 cm sheet]) is placed on the tip of the pipet tube as the web (106) and is fastened into place by gently sliding the collar (107) over it. The collar (107) is positioned about 1-2 mm from the end allowing the glass fiber web (106) to extend beyond the collar (107).

A third transfer pipet is cut to create a scoop for diatomaceous earth (Eagle-Picker Celatom Diatomite L-100). The bowl portion is cut diagonally with a portion of the tip cut away to make a larger exit funnel. Diatomaceous earth is scooped into the bowl portion and tapped in the pipet through the pipet stem. The pipet is filled past the stem into the bowl portion and is tapped vertically and from the side. About a 5% settling is observed. A cotton plug (105) is then inserted in the bowl over the diatomaceous earth.

EXAMPLE 3

The device is constructed as in Example 2 except that Hydrophilic HDC 8G (Pall BioSupport Corp., Glen Cove, N.Y., Catalog No. P/N M-1026B) is used instead of glass fiber for the web (106).

EXAMPLE 4

The device is constructed as in Example 2 except that 5.0 micron LoProdyne (Pall BioSupport Corp., Glen Cove, N.Y., Catalog No. P/N LNCGR) is used instead of glass fiber for the web (106).

EXAMPLE 5

The device is constructed as in Example 2 except that Hydrophilic HDC 8G (Example 3) and LoProdyne (Example 4) are used together as the web (106). This is the preferred embodiment and involves using LoProdyne in front (i.e. toward the liquid receiving end (103)) with the Hydrophilic HDC 8G as a backing. It has been observed that in this arrangement, the web (106) is better in its ability to capture latex beads.

EXAMPLE 6

Figure 2:
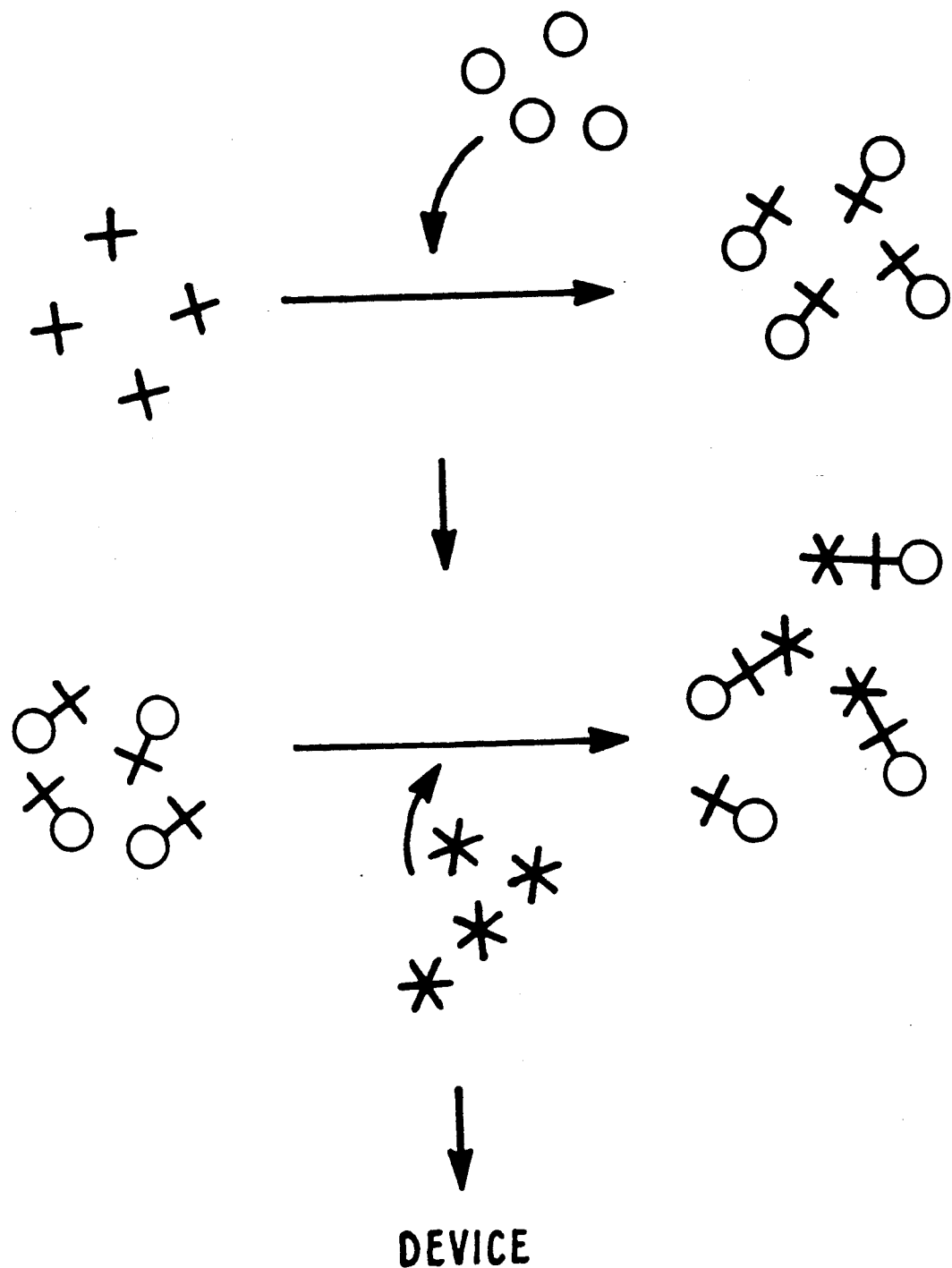
FIG. 2 is a schematic representation of the steps of one embodiment of the method of the present invention.

FIG. 2 is a schematic representation of the steps of the method of the present invention. A first molecule (+) is attached to a solid support (O) so as to make a solid support conjugate (O+). The solid support conjugate (O+) is allowed to react with free, unconjugated molecules (*) in a reaction vessel (shown schematically). These free, unconjugated molecules (*) can be any type of molecule except they are not identical to the molecules (+) attached to the solid support (O) so as to make a solid support conjugate (O+). The reaction mixture, containing 1) unconjugated molecules bound to the solid support conjugate (O+*), 2) free, unconjugated molecules (*) and 3) unreacted solid support conjugate (O+), is then brought in contact with the device.

Figure 3A:
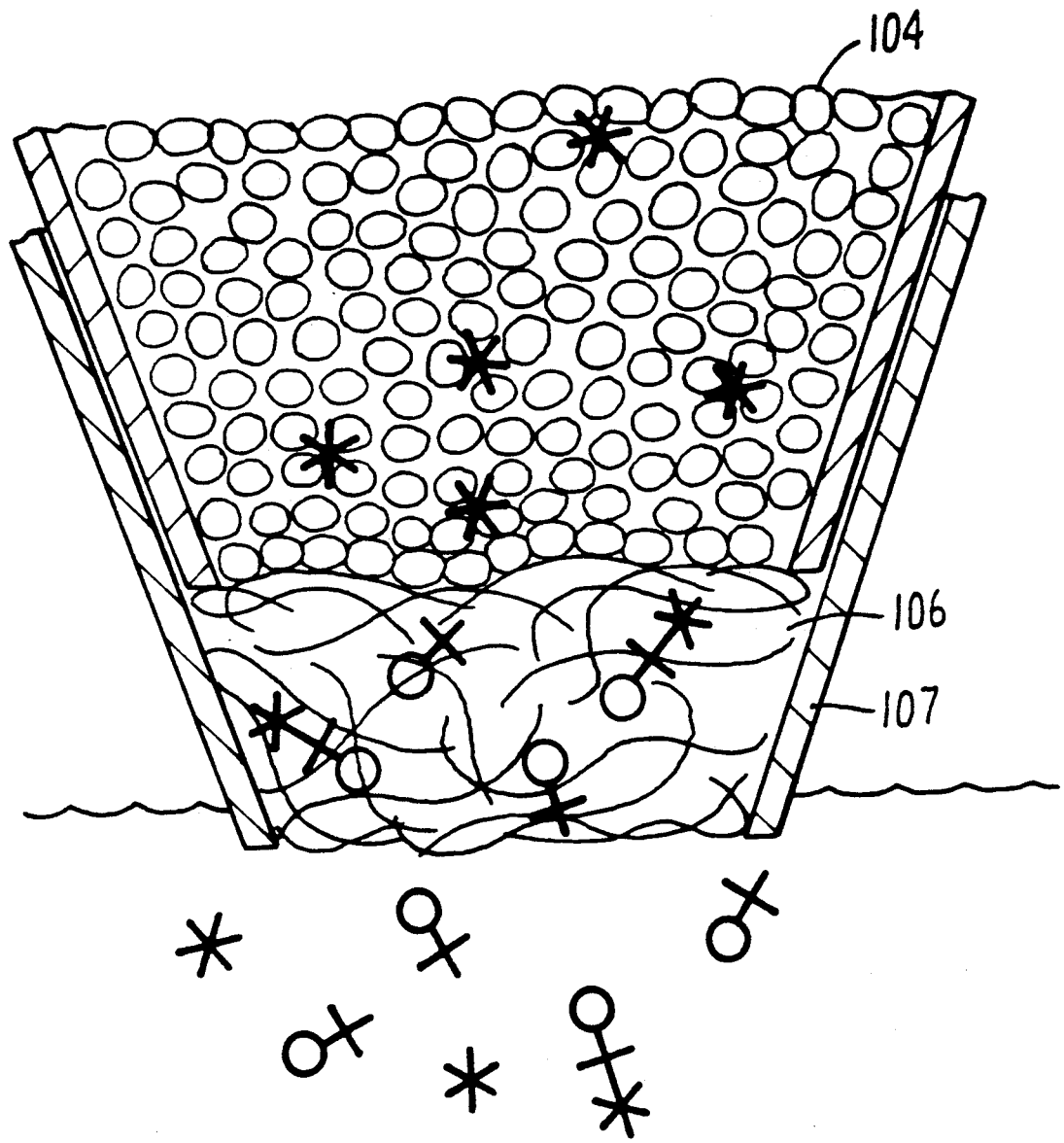
FIGS. 3A and 3B show the embodiment depicted in FIG. 1 in operation.

In operation (FIG. 3A), liquid (110) is contacted at the liquid receiving end (103) of the container (101). The absorbent material (104) serves to pull liquids upwards, against gravity, by capillary action. In so doing, the absorbent material (104) causes a flow of reactants (O+, *, O+*) through the receiving end (103) into the web (106). In the preferred embodiment, the solid support (O) is made of latex beads and the web (106) is either HDC 8G (Example 3) or 5.0 micron LoProdyne (Example 4). In both cases, the web (106) serves to isolate and capture latex beads through charge interactions.

After the reactants are drawn into the device, it may be desirable to bring a wash solution into contact with the device. This step (not shown) will assure that no unbound molecules (*) are in the area of the web (106).

Figure 3B:
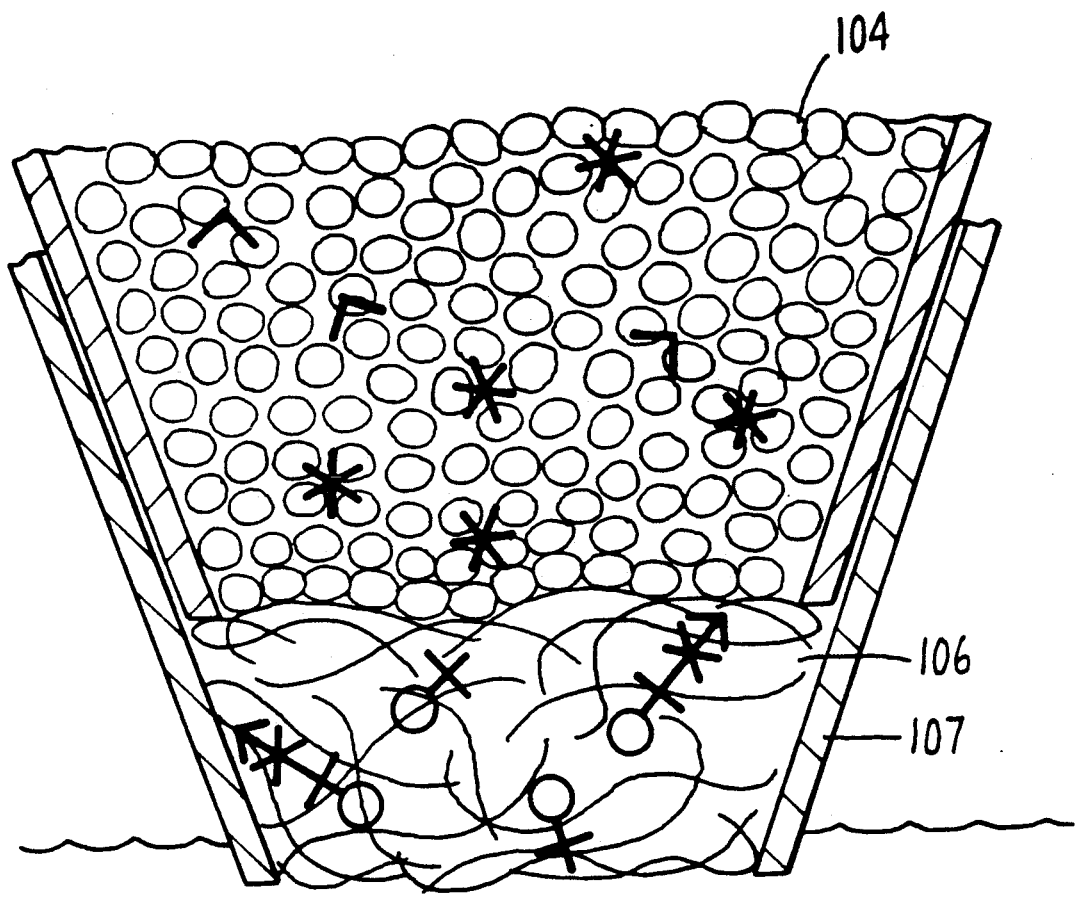

The final steps in the method of the present invention involve signal generation and measurement. With the solid support conjugates (O+) trapped on the web (106), a means for signaling the presence of and measuring the quantity of molecules bound to the solid support conjugate (O+*) is provided. In one embodiment (FIG. 3B), this means comprises contacting the device with a liquid (111) containing yet another molecule (>) with affinity for the unconjugated molecules (*) so as to form a reaction complex (O+*>). This second molecule (>) can be identical to the first molecule (+) or it can be nonidentical. This second molecule (>) can contain a label (radioactive, fluorescent, etc.) or can, itself, be conjugated with a signal producing enzyme prior to contact with the device. In this latter case, contact of the device with a liquid containing the second molecule (>) is followed by 1) contact of the device with a wash solution, and 2) contact of the device with a liquid containing substrate for the signal producing enzyme (not shown).

EXAMPLE 7

Latex beads are used as the solid support. A first antibody with affinity for luteinizing hormone (LH) is attached to the latex beads so as to make a solid support conjugate (latex conjugate). A second antibody with affinity for LH is conjugated to alkaline phosphatase (enzyme conjugate) for signal generation.

A tissue culture 24 well plate is used as a reaction vessel. Canine urine containing LH is used as a source of LH (positive sample) and canine urine without LH is used as a negative control (negative sample).

For the reaction, 50 μl of 0.4% latex conjugate is placed in wells A-1 and C-1 of the 24 well plate. The positive sample (1 ml) is then added to A-1. The negative sample (1 ml) is then added to C-1. The reaction is timed for 15 minutes. Two identical assay devices (Example 1) are, thereafter, inserted into the reaction mixture and the reaction mixture is, thereby, pulled into the diatomaceous earth matrix until all of the liquid is absorbed.

Enzyme conjugate (50 μl) (diluted to 1:15 and filtered through a Unipore 0.2μ in-line filter) is pipetted into new wells A-2 and C-2. The devices are placed into the new wells and the enzyme conjugate solution is absorbed. Binding is allowed to take place over a 2 minute period.

The web (106) is then washed with 1 ml of wash solution placed in wells A-3 and C-3. After the wash solution is absorbed, 1 drop (approximately 50 μl) of color development reagent is added to wells A-4 and C-4, and the devices are shifted to theses new wells. The color development proceeds for 2 minutes and then is stopped using 4 drops of stop reagent in wells A-5 and C-5.

The result for this LH assay showed an intense and readily apparent color development over a large area in and around the web (106) of the device where positive sample was introduced. On the other hand, no signal was apparent from the device where negative sample was introduced. No hint of residual conjugate is present to give background color development. Importantly, the matrix appeared to be of sufficient size to absorb the volume of liquid used; there was no sign of liquid dripping back through the web (106).

From the above examples, it is clear that the direction of reagent flow is a major difference between the present invention and the inventions of others. Instead of migrating downward through a matrix by gravity, the reactants of the present invention are drawn upward through the device against the force of gravity. An absorbent material (104) such as diatomaceous earth provides one mechanism for drawing the liquid medium, i.e. capillary action. This creates a steady, smooth flow gently depositing solid support conjugates (O+) such as latex beads onto the web (106) which acts both as an absorbent/adsorbent for the latex beads and as a membrane septum to retain the diatomaceous earth in the tube. A gentle flow is critical since the solid support conjugates are preferably trapped and held by a charge interactions in the web (106). Fast flows will sweep the solid support conjugates (O+) past the web (106). Furthermore, a flow that is too slow may result in insufficient washing of the web (106) due to diffusion of unbound additional binding molecules (>).

Thus it can be seen that the present invention provides a novel and improved method for detecting molecules in a liquid medium. It should be understood that various alternatives to the methods and materials herein disclosed may be employed in practicing the present invention. It is intended that the following claims define the invention, and that the materials and methods within the scope of these claims and their equivalents be covered thereby.

What is claimed is:

1. A method of performing an assay that detects unconjugated molecules in a liquid medium by their binding to solid support conjugates contained and in liquid medium comprising:
   a) contacting said liquid medium with an assay device;
   b) drawing said liquid medium against the force of gravity through said device;
   c) trapping the solid support conjugates drawn into assay device; and
   d) detecting the unconjugated molecules bound to said trapped solid support conjugates.

2. A method as in claim 1 wherein said drawing comprises capillarily absorbing said liquid medium into an absorbent matrix housed in said assay device.

3. In a method of performing an assay that detects unconjugated molecules in a liquid medium by their binding to solid support conjugates contained in said liquid medium, wherein said solid support conjugates are allowed to react with said unconjugated molecules in said liquid medium so as to form a reaction mixture containing (i) unconjugated molecules bound to said solid support conjugates, (ii) unreacted, solid support conjugates, and (iii) free, unconjugated molecules, wherein said bound, unconjugated molecules and said free, unconjugated molecules species are separated, and wherein said bound species is detected and measured; the improvement which comprises accomplishing said separation of said bound, unconjugated molecules and said free, unconjugated molecules by contacting at least a portion of said reaction mixture subsequent to formation thereof, with a device comprising (1) a container, (2) material housed in said container which is capillarily absorbent relative to said reaction mixture, said material being positioned above (3) a web which is capable of trapping said (i) unconjugated molecules bound to said solid support conjugates and said (ii) unreacted, solid support conjugates, and which is permeable to said (iii) free, unconjugated molecules, whereby said at least a portion of said reaction mixture is drawn into said device against the force of gravity by capillary action and said (i) unconjugated molecules bound to said solid support conjugates and said (ii) unreacted, solid support conjugates remain in the web and said free, unconjugated molecules proceed into said material.

* * * * *

UNITED STATES PATENT AND TRADEMARK OFFICE
CERTIFICATE OF CORRECTION

PATENT NO. : 5,106,761
DATED : 04/21/92
INVENTOR(S) : ANDREW H. KUNIYUKI

It is certified that error appears in the above-identified patent and that said Letters Patent is hereby corrected as shown below:

In Column 1, line 7 please delete "inventions" and replace with --invention--.

In Column 1, line 43 please delete "passed" and replace with --pass--.

In Column 3, line 36 please delete "are" and replace with --is--.

In Column 6, line 65 please delete "theses" and replace with --these--.

In Column 8, line 31 please insert --,-- after "container".

Signed and Sealed this

Seventh Day of December, 1993

Attest:

BRUCE LEHMAN

*Attesting Officer*  *Commissioner of Patents and Trademarks*